United States Patent [19]
Sekine et al.

[11] Patent Number: 6,150,425
[45] Date of Patent: Nov. 21, 2000

[54] O/W/O TYPE MULTIPHASE EMULSION

[75] Inventors: Tomoko Sekine; Fumiaki Matsuzaki; Toshio Yanaki; Michihiro Yamaguchi, all of Yokohama, Japan

[73] Assignee: Shiseido Company, Ltd., Tokyo, Japan

[21] Appl. No.: 09/147,821

[22] PCT Filed: Jul. 15, 1998

[86] PCT No.: PCT/JP98/03187

§ 371 Date: Mar. 15, 1999

§ 102(e) Date: Mar. 15, 1999

[87] PCT Pub. No.: WO99/03572

PCT Pub. Date: Jan. 28, 1999

[30] Foreign Application Priority Data

Jul. 17, 1997 [JP] Japan ................................ 9-208458
Jul. 17, 1997 [JP] Japan ................................ 9-208459

[51] Int. Cl.$^7$ .............................. A61K 9/113; B01F 3/08; B01F 17/28; B01F 17/54
[52] U.S. Cl. ......................... 516/22; 424/401; 426/602; 514/941; 514/943; 514/944; 514/975; 516/902
[58] Field of Search ............... 516/22, 902; 514/941, 514/943, 944, 975; 424/401

[56] References Cited

U.S. PATENT DOCUMENTS

| | | | |
|---|---|---|---|
| 4,328,149 | 5/1982 | Morse et al. ................... | 524/801 X |
| 4,675,179 | 6/1987 | Suzuki et al. ................... | 514/941 X |
| 5,015,469 | 5/1991 | Yoneyama et al. .............. | 516/22 X |
| 5,178,871 | 1/1993 | Thill ................................ | 514/941 X |
| 5,391,321 | 2/1995 | Grüning et al. .................. | 516/22 |
| 5,693,255 | 12/1997 | Okamoto et al. ................ | 514/943 X |
| 5,849,315 | 12/1998 | Rerek et al. ..................... | 514/944 X |
| 5,876,702 | 3/1999 | Gers-Barlag et al. ........... | 424/401 X |
| 5,925,364 | 7/1999 | Ribier et al. ..................... | 514/941 X |
| 5,985,177 | 11/1999 | Yoshida et al. .................. | 424/401 X |

FOREIGN PATENT DOCUMENTS 8-323188  12/1996  Japan.

*Primary Examiner*—Richard D. Lovering
*Attorney, Agent, or Firm*—Townsend & Banta

[57] ABSTRACT

An O/W/O type multiple emulsion in which an O/W type emulsion is dispersed in the outer phase oil wherein the O/W type emulsion in the inner phase contains water, an oil based ingredient, a surfactant and an amphiphilic substance chosen from those which can form a gel at ordinal temperature or higher in an amphiphilic substance-surfactant-oil-water system or N-long chain acyl acidic amino acid monosalt and an amphiphilic substance chosen from those which can form a gel at ordinal temperature or higher in an amphiphilic substance-N-long chain acyl acidic amino acid monosalt-oil-water system, said outer phase oil contains organophilic modified clay minerals and an emulsifying agent with a HLB of 7 or lower, and the weight ratio of the O/W type emulsion and the outer phase oil is 2:3–19:1. An O/W/O type multiple emulsion with superior stability over time and good usability.

53 Claims, 3 Drawing Sheets

O/W/O TYPE MULTIPHASE EMULSION

This application is a 371 of PCT/JP98/03187 filed Jul. 15, 1998, which claims priority based on Japanese patent applications 9-208458 and 9-208459, both filed on Jul. 17, 1997.

FIELD OF THE INVENTION

This invention relates in general to an O/W/O type multiple emulsion and more particularly to an O/W/O type multiple emulsion obtained by dispersing an O/W type emulsion in the outer phase oil which has superior stability over time.

BACKGROUND OF THE INVENTION

The oil-in-water-in-oil type emulsified composition obtained by further emulsifying and dispersing an oil-in-water type emulsified composition (hereafter referred to as O/W type emulsion) in the oil phase is called an O/W/O type multiple emulsion and has become important in various industrial applications such as cosmetics, food, and medicines.

Figure 1:
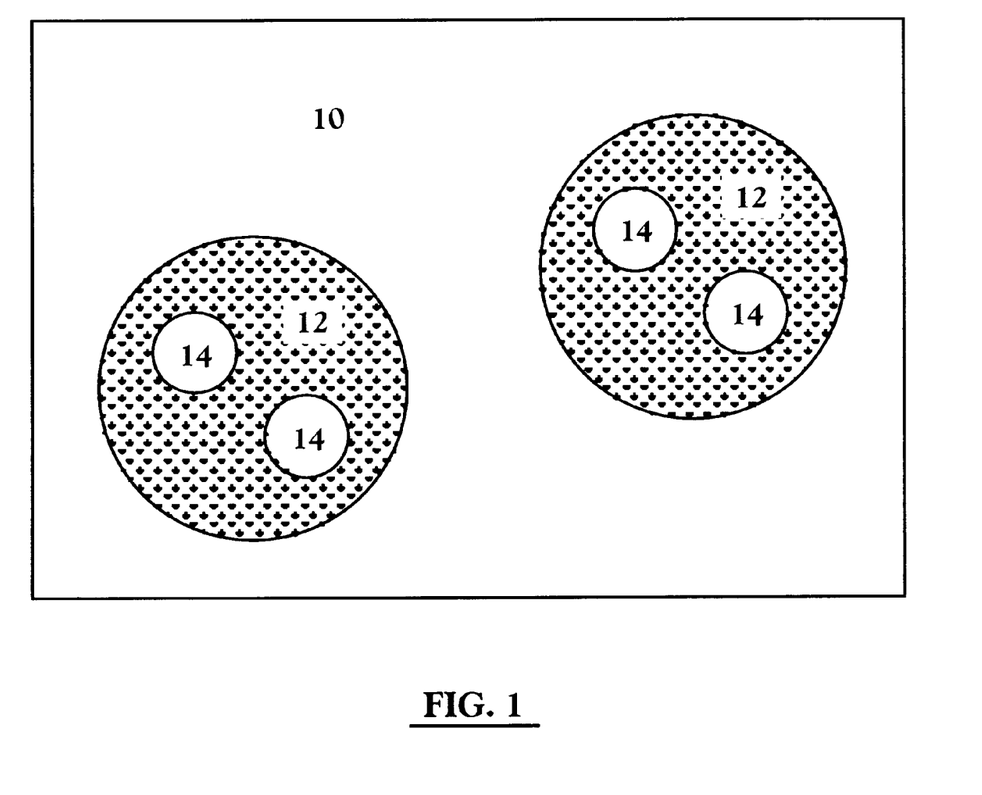
FIG. 1 is a conceptual illustration of an O/W/O type multiple emulsion.

That is, while a usual O/W type emulsion is obtained by simply dispersing the oil phase in the water phase, the particle structure of an O/W/O type multiple emulsion comprises an inner phase oil 14 dispersed in a water phase 12 dispersed in an outer phase 10, as shown in FIG. 1.

Because of this, a special touch during use can be achieved which cannot be obtained by a simple O/W type or W/O type emulsion.

As a means to obtain a stable multiple emulsion, Japanese unexamined patent publication Tokkai Hei 8-323188, for example, describes a process in which a hydrophilic non-ionic surfactant is used to prepare the O/W type fine emulsion which is to be the inner phase, and this O/W type emulsion is dispersed and emulsified in the oil based ingredient containing an organophilic modified clay mineral which is to be the outer phase oil. The multiple emulsion obtained with this preparation method is known to suppress the merging of the inner phase oil and the outer phase oil and have significantly increased stability over time.

However, although solid and/or semi-solid oil ingredients such as higher alcohols and waxes are blended in to improve the skin-compatibility of a cream, in the case of the aforementioned O/W/O type multiple emulsion which contains the organophilic modified clay minerals in its outer phase oil, there is a problem in that blending these solid and/or semi-solid oil ingredients in the outer phase oil or the inner O/W type emulsion emulsified by using a nonionic surfactant degrades the stability over time.

Based on the aforementioned consideration, the inventors conducted earnest research to obtain a stable O/W/O type multiple emulsion and discovered that solid or semi-solid oil ingredients can be blended in the inner phase O/W type emulsion in a stable manner and an O/W/O type multiple emulsion with superior stability over time and improved skin-compatibility of the base into the skin can be obtained by adding an amphiphilic substance and surfactant of a specific combination to the O/W type emulsion, adding an organophilic modified clay mineral and an emulsifying agent with a HLB of 7 or less to the outer phase oil, and then dispersing the O/W type emulsion in the outer phase oil at a specific weight ratio, thus completing the present invention.

Also, based on the aforementioned consideration, the inventors conducted earnest research to obtain a stable O/W/O type multiple emulsion and discovered that solid or semi-solid oil ingredients can be blended in the inner phase O/W type emulsion in a stable manner and an O/W/O type multiple emulsion with superior stability over time and improved skin-compatibility of the base into the skin can be obtained by adding an amphiphilic substance and N-long chain acyl acidic amino acid monosalt of a specific combination to the O/W type emulsion, adding an organophilic modified clay mineral and an emulsifying agent with a HLB of 7 or less to the outer phase oil, and then dispersing the O/W type emulsion in the outer phase oil at a specific weight ratio, thus completing the present invention.

The object of the present invention is to provide an O/W/O type multiple emulsion which exhibits superior stability over time even when a solid or semi-solid ingredient is added to improve the usability and dies not limit the selection of the oil ingredient to be contained in the O/W type emulsion which is to be the inner phase.

DISCLOSURE OF THE INVENTION

That is, the first invention of the present application provides an O/W/O type multiple emulsion in which an O/W type emulsion is dispersed in the outer phase oil wherein the O/W type emulsion in the inner phase contains water, an oil based ingredient, a surfactant and an amphiphilic substance chosen from those which can form a gel at ordinal temperature or higher in an amphiphilic substance-surfactant-oil-water system, said outer phase oil contains organophilic modified clay minerals and an emulsifying agent with a HLB of 7 or lower, and the weight ratio of the O/W type emulsion and the outer phase oil is 2:3–19:1.

Also, the present invention provides the afforementioned O/W/O type multiple emulsion wherein said amphiphilic substance is composed of a higher fatty acid and/or higher alcohol whose carbon chain has a carbon number of 12 or more.

Furthermore, the present invention provides the aforementioned O/W/O type multiple emulsion wherein the surfactant contained in said inner phase O/W type emulsion is composed of a metal soap of a higher fatty acid.

Also, the present invention provides the aforementioned O/W/O type multiple emulsion wherein said organophilic modified clay minerals are obtained by treating a water swelling clay mineral with a quaternary ammonium type cation surfactant and a nonionic surfactant.

Also, the present invention provides the aforementioned O/W/O type multiple emulsion wherein the amphiphilic substance contained in the O/W type emulsion dispersed in said outer phase oil is a higher alcohol and higher fatty acid, the surfactant is a metal soap prepared by neutralizing said higher fatty acid, and said amphiphilic substance is contained in the inner phase oil of the O/W type emulsion in the amount of 0.1–80 wt %.

Furthermore, the present invention provides a method of preparing the O/W/O type multiple emulsion comprising a process in which the oil based ingredient which is to be the inner oil is added to an aqueous solution containing a neutralizing agent and the O/W type emulsion is prepared by a high pressure emulsification treatment or an ultrasonic emulsification treatment and a process in which said O/W type emulsion is dispersed and emulsified in the oil based ingredient which is to be the outer phase oil and contains an organophilic modified clay minerals and an emulsifying agent with a HLB of 7 or less.

The second invention of the present application provides an O/W/O type multiple emulsion in which an O/W type emulsion is dispersed in the outer phase oil wherein the O/W type emulsion in the inner phase contains water, an oil based ingredient, N-long chain acyl acidic amino acid monosalt and an amphiphilic substance chosen from those which can form a gel at ordinal temperature or higher in an amphiphilic substance-N-long chain acyl acidic amino acid monosalt-oil-water system, said outer phase oil contains organophilic modified clay minerals and an emulsifying agent with a HLB of 7 or lower, and the weight ratio of the O/W type emulsion and the outer phase oils is 2:3–19:1.

Also, the present invention provides the afforementioned O/W/O type multiple emulsion wherein said amphiphilic substance is composed of a higher fatty acid and/or higher alcohol whose carbon chain has a carbon number of 12 or more.

Furthermore, the present invention provides the aforementioned O/W/O type multiple emulsion wherein the N-long chain acyl acidic amino acid monosalt contained in said inner phase O/W type emulsion is N-stearoyl-L-glutamic acid monosalt.

Also, the present invention provides the aforementioned O/W/O type multiple emulsion wherein said inner phase O/W type emulsion contains an N-long chain acyl acidic amino acid disalt and its content is such that the mole ratio is 0.25 or less of that of the N-long chain acyl acidic amino acid monosalt.

Furthermore, the present invention provides the aforementioned O/W/O type multiple emulsion wherein wherein the content of the inner phase oil in the O/W type emulsion is half or more of the total of said amphiphilic substance and N-long chain acyl acidic amino acid monosalt.

Also, the present invention provides the aforementioned O/W/O type multiple emulsion wherein said amphiphilic substance and the N-long chain acyl acidic amino acid monosalt are present on the oil drop interface of the O/W type emulsion and the amount measured by using the DSC peak area ratio is 90% or more of the total content.

Furthermore, the present invention provides the aforementioned O/W/O type multiple emulsion wherein the total amount of said amphiphilic substance and the N-long chain acyl acidic amino acid monosalt is 0.2 wt % or more of the water phase of the O/W type emulsion.

Also, the present invention provides the aforementioned O/W/O type multiple emulsion wherein said organophilic modified clay minerals are obtained by treating a water swelling clay mineral with a quaternary ammonium type cation surfactant and a nonionic surfactant.

Furthermore, the present invention provides a method of preparing the O/W/O type multiple emulsion comprising a process in which the oil based ingredient which is to be the inner oil is added to the water phase containing an N-long chain acyl acidic amino acid monosalt and then the O/W type emulsion is prepared by a high pressure emulsification treatment or an ultrasonic emulsification treatment and a process in which said O/W type emulsion is dispersed and emulsified in the oil based ingredient which is to be the outer phase oil and contains an organophilic modified clay minerals and an emulsifying agent with a HLB of 7 or less.

THE BEST MODES OF THE EMBODIMENTS

The configuration of the present invention is described in detail below. First, items which are specific to the first invention of the present application are described.

The amphiphilic substance which is blended in the O/W type emulsion which is used for the inner phase in the present invention is a substance which is surface-active but not as strongly surface-active as common surfactant due to its stronger hydrophobicity. Examples include higher alcohols such as cetanol and stearyl alcohol, higher fatty acids such as myristic acid, palmitic acid, stearic acid, behenic acid, isostearic acid, oleic acid, linolenic acid, linolic acid, and oxystearic acid, esters such as isopropyl myristate, isopropyl palmitate, isopropylisostearate, and glyceryl 2-ethylhexanoate, higher aliphatic alcohols, monoglyceride, glycerolmonoalkyl ether, monoalkylamine, and compounds with a sterol frame (cholesterol and phytosterol). Preferably used are higher alcohols and/or higher fatty acids with a carbon number of 12 or higher, more preferably 16 or higher.

The surfactant blended in the O/W type emulsion is an anionic surfactant, cationic surfactant, ampholytic surfactant, or a hydrophilic or lipophilic nonionic surfactant. Specifically, a metal soap of a higher fatty acid is preferable.

Examples of the anionic surfactant include fatty acid soaps including soap base, sodium laurate and sodium palmitate, higher alkylsulfuric ester salts including sodium laurylsulfate and potassium laurylsulfate, alkyl ether sulfuric ester salts including triethanolamine POE laurylsulfate and sodium POE laurylsulfate, N-acylsarcosinic acids including sodium lauroylsarcosinate, higher fatty acid amide sulfonates including sodium N-myristoyl-N-methyltaurate, sodium methyltaurate cocoate and sodium laurylmethyltaurid, etc., phosphoric ester salts including sodium POE oleyl ether phosphate and POE stearyl ether phosphoric acid, etc., sulfosuccinates including sodium di-2-ethylhexylsulfosuccinate, sodium monolauroylmonoethanolamide-polyoxyethylenesulfosuccinate and sodium laurylpolypropylene glycol sulfosuccinate, etc., alkylbenzenesulfonates including sodium linear dodecylbenzenesulfonate, triethanolamine linear dodecylbenzenesulfonate and linear dodecylbenzenesulfonic acid, N-acylglutamates including monosodium N-lauroylglutamate, disodium N-stearoylglutamate and monosodium N-myristoyl-L-glutamate, etc., higher fatty acid ester sulfates including sodium hydrogenated glyceryl cocoate sulfate, sulfated oils including turkey red oil, as well as POE alkyl ether carboxylate, POE alkylaryl ether carboxylate, α-olefinsulfonates, higher fatty acid ester sulfonate, sec-alcohol sulfate, higher fatty acid alkyloyl amide sulfate, sodium lauroyl monoethanolamide N-succinate, di(triethanolamine)-N-palmitoylaspartate and sodium caseinate.

Examples of the cationic surfactant include alkyltrimethyl ammonium salts including stearyltrimethyl ammonium chloride and lauryltrimethyl ammonium chloride, distearyl dimethyl ammonium chloride/dialkyl dimethyl ammonium chloride, alkylpyridinium salts including poly (N,N-dimethyl-3,5-methylene piperidinium chloride) and cetyl pyridinium chloride, etc., as well as alkyl quaternary ammonium salt, alkyldimethylbenzyl ammonium salt, alkylisoquinolinium salt, dialkylmorpholinium salts, POE alkylamine, alkylamine salt, polyamine fatty acid derivatives, amylalcohol fatty acid derivatives, benzalkonium chloride and benzetonium chloride.

Examples of the ampholytic surfactant include imidazoline type ampholytic surfactants including 2-undecyl-N,N, N-(hydroxyethylcarboxymethyl)-2-imidazoline sodium salt and 2-cocoyl-2-imidazaliniumhydroxide-1-carboxyethyloxy 2 sodium salts etc. and betaine type surfactants including 2-heptadecyl-N-carboxymethyl-N-hydroxyethyl imidazolinium betaine, betaine lauryldimethylamino acetate, alkyl betaine, amide betaine and sulfobetaine.

Examples of the lipophilic non-ionic surfactant include sorbitan fatty acid esters including sorbitan monooleate, sorbitan monoisostearate, sorbitan monolaurate, sorbitan monopalmitate, sorbitan monostearate, sorbitan sesquioleate, sorbitan trioleate, diglycerolsorbitan penta-2-ethylhexylate and diglycerolsorbitan tetra-2-ethylhexylate, etc., glycerine polyglycerine fatty acids including mono-cottonseed-fatty acid glyceryl ester, glyceryl monoerucate, glyceryl sesquioleate, glyceryl monostearate, glyceryl α, α'-oleate pyroglutamate and glyceryl monostearate monomalate, propylene glycol fatty acid esters including propylene glycol monostearate, as well as hydrogenated castor oil derivatives, and glycerol alkyl ether.

Examples of the hydrophilic non-ionic surfactant include POE sorbitan fatty acid esters including POE-sorbitan monooleate, POE-sorbitan monostearate, POE-sorbitan monooleate and POE-sorbitan tetraoleate, POE-sorbitol fatty acid esters including POE-sorbitol monolaurate, POE-sorbitol monooleate, POE-sorbitol pentaoleate and POE-sorbitol monostearate, etc., POE-glycerol fatty acid esters including POE-glyceryl monostearate, POE-glyceryl monoisostearate and POE-glyceryl triisostearate, POE fatty acid esters including POE monooleate, POE distearate, POE monodioleate and ethylene glycol distearate; POE alkyl ethers including POE lauryl ether, POE oleyl ether, POE stearyl ether, POE behenyl ether, POE 2-octyldodecyl ether and POE cholestanol ether, POE alkylphenyl ethers including POE octylphenyl ether etc., POE nonylphenylether and POE dinonylphenyl ether, pluaronics including pluronic, POE-POP alkyl ethers including POE-POP cetyl ether. POE-POP 2-decyltetradecyl ether, POE-POP monobutyl ether, POE-POP lanolin hydrate and POE-POP glycerol ether, tetra POE-tetra POP ethylenediamine condensates including tetronic, etc., POE castor oil hydrogenated castor oil derivatives including POE castor oil, POE hydrogenated castor oil, POE hydrogenated castor oil monoisostearate, POE hydrogenated castor oil triisostearate, POE hydrogenated castor oil monopyroglutamate monoisostearate diester, POE hydrogenated castor oil maleate, etc., POE beeswax/lanolin derivatives including POE sorbitol beeswax, etc., alkanol amides including coconut fatty acid diethanol amide, lauric acid monoethanol amide and fatty acid isopropanol amide; as well as POE propylene glycol fatty acid ester, POE alkyl amine, POE fatty acid amide, sucrose fatty acid ester, POE nonylphenylformaldehyde condensate, alkylethoxydimethylamine oxide and trioleyl phosphate.

The present invention uses a combination of the amphiphilic substance-surfactant which forms a gel at ordinal temperature or higher in an amphiphilic substance-surfactant-oil-water system, chosen from the aforementioned amphiphilic substances and surfactants. The selection of the combination of the amphiphilic substance-surfactant which forms a gel in a water system at ordinal temperature or higher is not limited in particular as long as each blend ratio used allows formation of a gel.

Preferable combinations are behenic acid and/or behenyl alcohol (amphiphilic substance)-behenic acid/potassium hydroxide fatty acid soap (surfactant), stearic acid and/or stearyl alcohol (amphiphilic substance)-stearic acid/potassium hydroxide fatty acid soap (surfactant), stearyl alcohol (amphiphilic substance)-sodium cetylsulfate (surfactant), behenyl alcohol (amphiphilic substance)-behenyltrimethylammonium chloride (surfactant), and behenyl alcohol (amphiphilic substance)-stearyltrimethylammonium chloride (surfactant). In the present invention, although the amphiphilic substance and the surfactant can be separately blended in the O/W type emulsion, it is preferable to blend in a higher fatty acid which is an amphiphilic substance and a neutralizer such as potassium hydroxide so that the emulsion contains the amphiphilic substance and a surfactant composed of a higher fatty acid soap.

The most preferable combination is a higher alcohol and higher fatty acid and potassium hydroxide fatty acid soap obtained by blending in an amphiphilic substance composed of a higher alcohol and a higher fatty acid and potassium hydroxide in a mole amount less than that of the higher fatty acid.

The blend ratio of the amphiphilic substance is preferably 25 wt % or less, more preferably 10 wt % or less, of the total amount of the O/W type emulsion. The blend ratio of the surfactant is preferably 20 wt % or less, more preferably 10 wt % or less, of the total amount of the O/W type emulsion.

The amount of the inner phase oil in the O/W type emulsion is half or more, preferably an equal amount or more, of the total amount of the amphiphilic substance and the surfactant. If the amount of the oil phase is less than half of the amphiphilic substance, then the emulsification stability over time tends to become poor.

For the O/W type emulsion, the weight ratio of the oil phase: the water phase is preferably less than 1:1 so there is less of the oil phase.

Next, items which are specific to the second invention of the present application are described below.

The amphiphilic substance which is blended in the O/W type emulsion which is used for the inner phase in the present invention is a substance which is surface-active but not as strongly surface-active as a common surfactant due to its hydrophobicity. Examples for use as the amphiphilic substance include a higher fatty acid, higher aliphatic alcohol, monoglyceride, glycerol monoalkyl ether, monoalkyl amine, sterols, and a free-type N-long chain acyl acidic amino acid. Preferable are a higher fatty acid, higher aliphatic alcohol, and an N-long chain acyl acidic amino acid. Particularly preferable are a higher fatty acid and/or higher aliphatic alcohol.

Preferable for the higher fatty acid and higher aliphatic alcohol are those with a carbon number of 12 or higher, more preferably 16 or higher. Preferable for the N-long chain acyl acidic amino acid are those with a long chain acyl group with a carbon number of 12 or higher, more preferably 16 or higher. A smaller carbon number may cause a problem in that sufficient emulsification stability cannot be achieved.

Examples for use as the higher fatty acid include lauric acid, myristic acid, palmitic acid, stearic acid, behenic acid, oleic acid, 12-hydroxystearic acid, undecylenic acid, tolic acid, isostearic acid, linolenic acid, linolic acid, eicosapentaenoic acid (EPA) and docosahexaenoic acid (DHA). Examples for use as the higher aliphatic alcohol include the higher alcohols corresponding to these higher fatty acids.

Examples for use as the N-long chain acyl acidic amino acid include N-stearoyl-L-glutamic acid, N-palmitoyl-L-glutamic acid, N-myristoyl-L-glutamic acid, N-lauryl-L-glutamic acid, N-cocoyl-L-glutamic acid, N-stearoyl-L-aspartic acid, N-palmitoyl-L-aspartic acid, N-myristoyl-L-aspartic acid, N-lauryl-L-aspartic acid, and N-cocoyl-L-aspartic acid, etc.

The "N-long chain acyl acidic amino acid monosalt" to be blended in the O/W type emulsion refers to an N-long chain acyl acidic amino acid which has one of its carboxyl groups neutralized to become a salt. An "N-long chain acyl acidic amino acid" is an amino acid composed of an acidic amino acid with its nitrogen atom covalently bonded to a long chain acyl group. The long chain acyl group bonded to the acidic amino acid can be either a linear or branched chain, and can be either saturated or unsaturated. The carbon number of the long chain acyl group is preferably 12 or more, and more preferably 16 or more. Those with a smaller carbon number, that is, a shorter chain, may not be able to achieve sufficient emulsification stability.

Examples for use as the N-long chain acyl acidic amino acid monosalt include N-stearoyl-L-glutamic acid monosalt, N-palmitoyl-L-glutamic acid monosalt, N-myristoyl-L-glutamic acid monosalt, N-lauryl-L-glutamic acid monosalt, N-cocoyl-L-glutamic acid monosalt, N-stearoyl-L-aspartic acid monosalt, N-palmitoyl-L-asparatic acid monosalt, N-myristoyl-L-aspartic acid monosalt, N-lauryl-L-aspartic acid monosalt, and N-cocoyl-L-aspartic acid monosalt. The selection of the counter ion for the N-long chain acyl acidic amino acid monosalt is not limited in particular. Preferable examples include sodium, potassium, and triethanolamine, etc.

Figure 2:
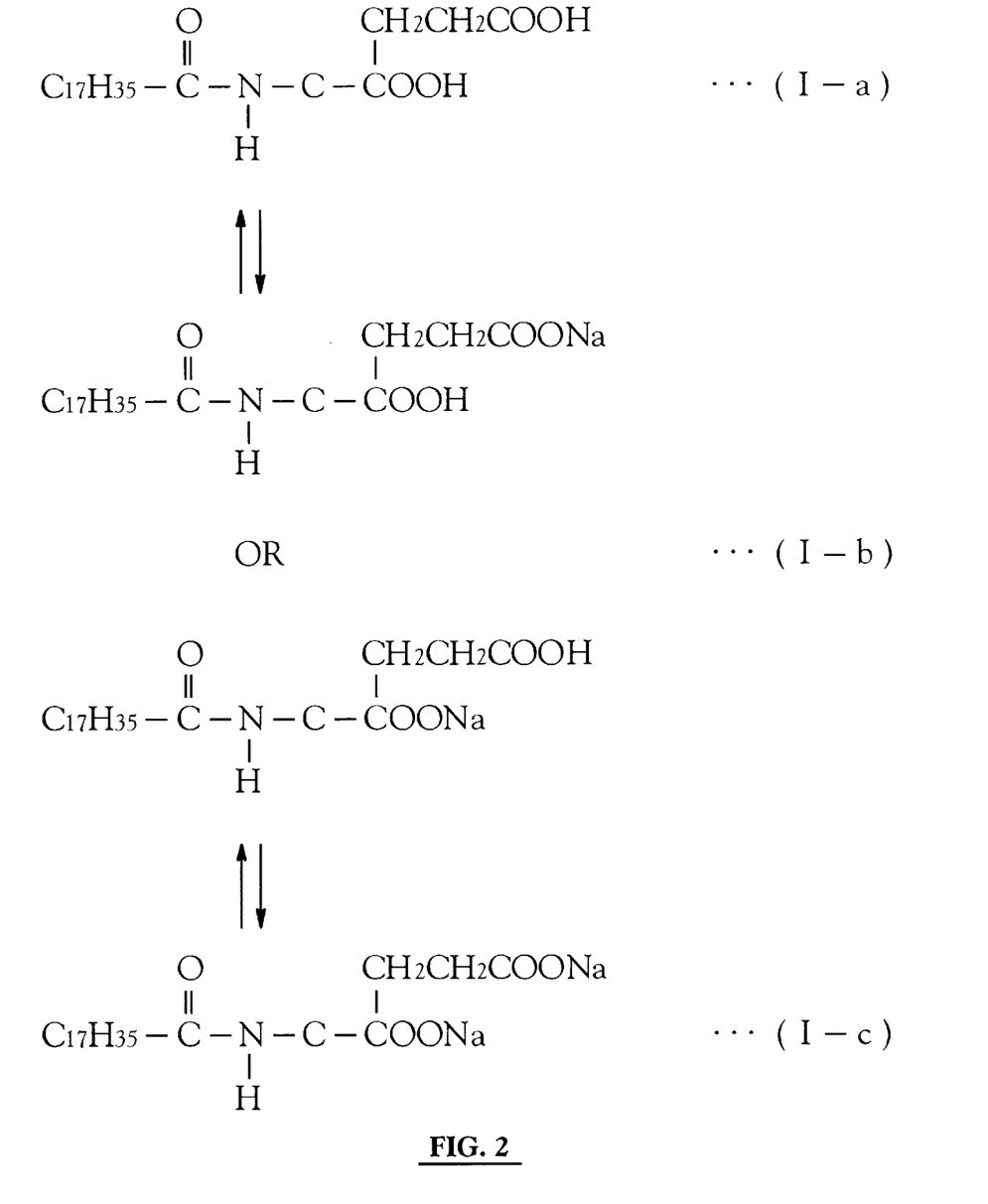
FIG. 2 illustrates the neutralization states of N-stearoyl-L-glutamic acid monosalt.

An N-long chain acyl acidic amino acid has at least two carboxyl groups in its molecular structure. In water, its form changes from the acidic type N-long chain acyl acidic amino acid to an N-long chain acyl acidic amino acid monosalt, and finally to an N-long chain acyl acidic amino acid disalt as the neutralization ratio of the carboxyl group increases. For example, if the N-long chain acyl acidic amino acid is N-stearoyl-L-glutamic acid, then there are one amino group and two carboxyl groups in one molecule. When the neutralization ratio is 0, all of the molecules are believed to exist as the acidic type as shown in (1-a) of FIG. 2. When an alkali, sodium hydroxide for example, is added to gradually neutralize it the ratio of the monosodium salt type (1-b) gradually increases and all the N-stearoyl-L-glutamic acid is believed to be the monosodium salt type (1-b) at a neutralization ratio of 50%. If sodium hydroxide is further added the monosodium salt type turns into the disodium salt type (1-c) and all the N-stearoyl-L-glutamic acid is believed to be the disodium salt type (1-c) at a neutralization ratio of 100%.

As described above, an N-long chain acyl acidic amino acid assumes different forms depending on its neutralization ratio. Also as described above, the acidic type of an N-long chain acyl acidic amino acid can be used for the amphiphilic substance of the present invention. For example, when alkali is additionally used such that the neutralization ratio of N-stearoyl-L-glutamic acid becomes 25%, the acidic type and the monosalt type of N-stearoyl-L-glutamic acid are believed to exist at a mole ratio of 1:1 and they can function as the amphiphilic substance and the N-long chain acyl acidic amino acid monosalt, respectively, for use in the present invention.

On the other hand, although an N-long chain acyl acidic amino acid disalt also forms a complex with the amphiphilic substance, this complex is weaker than the complex formed by the monosalt and the amphiphilic substance and cannot exhibit a sufficient effect. Also, use of the disalt would not be practical because the pH of the system would be in the strong alkaline range of 11 or higher. Therefore, when attempting to form an N-long chain acyl acidic amino acid monosalt in the system by separately adding an N-long chain acyl acidic amino acid and a neutralizing alkali, caution must be necessary because an excessive addition of alkali would increase the ratio of the N-long chain acyl acidic amino acid which exists in the disalt form and decrease the amount of the monosalt type.

The blend ratio of the alkali is preferably such that the mole ratio of the disalt is 0.25 times or less, more preferably 0.1 times or less, of that of the monosalt in the O/W type emulsion. If the amount of the disalt is larger then the pH of the system may not become weakly acidic, the pH stability and/or emulsification stability may decrease, and a cream-like touch may not be achieved when applied on the skin. Examples for use as the neutralizing alkali to neutralize the N-long chain acyl acidic amino acid include potassium hydroxide, sodium hydroxide, and triethanolamine.

The present invention uses a combination of the amphiphilic substance-N-long chain acyl acidic amino acid monosalt which forms a gel at ordinal temperature or higher in an amphiphilic substance-N-long chain acyl acidic amino acid monosalt-oil-water system, chosen from the aforementioned amphiphilic substances and N-long chain acyl acidic amino acid monosalts. The selection of the combination of the amphiphilic substance-N-long chain acyl acidic amino acid monosalt which forms a gel in a water system at ordinal temperature or higher is not limited in particular as long as each blend ratio used allows formation of a gel. A preferable combination is composed of a higher fatty acid and/or higher aliphatic alcohol with a carbon number of 12 or higher, more preferably 16 or higher, and N-stearoyl-L-glutamic acid monosalt.

Figure 3:
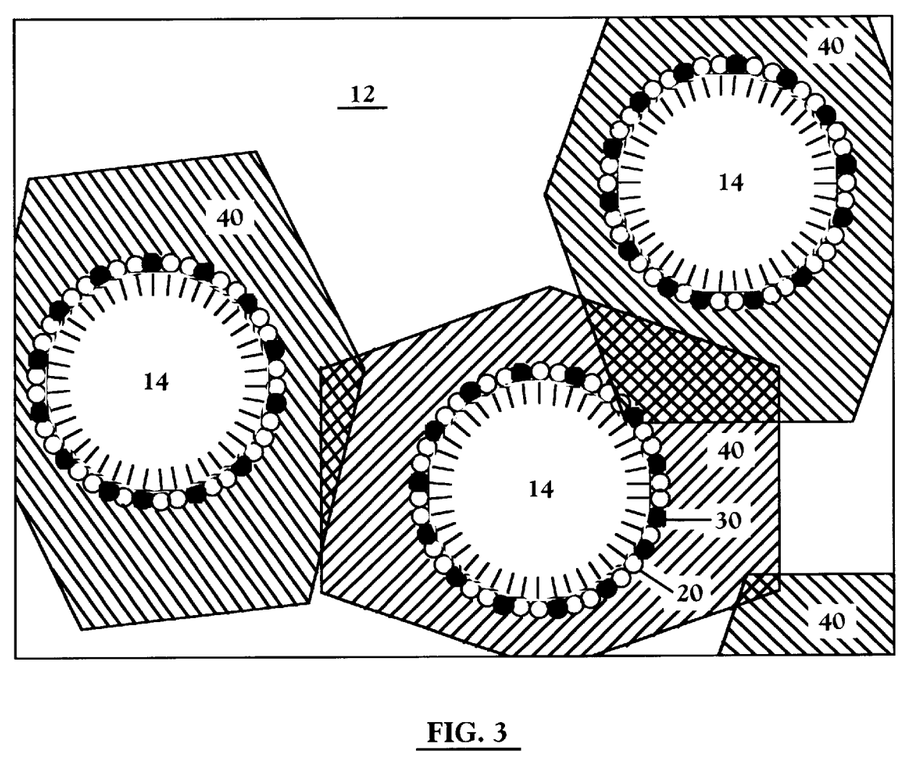
FIG. 3 is a conceptual illustration of the O/W type emulsion used in the present invention.

FIG. 3 is a conceptual illustration showing the O/W type emulsion. In FIG. 3, the oil phase 14 is dispersed in the water phase 12, and the amphiphilic substance 20 and the N-long chain acyl acidic amino acid monosalt 30 are present on the interface between said water phase 12 and the oil phase 14 to stabilize the dispersion state of oil phase 12 in water phase 10. Furthermore, N-long chain acyl acidic amino acid monosalt 30 and amphiphilic substance 20 are present in water phase 12 and a part of N-long chain acyl acidic amino acid monosalt 30 and amphiphilic substance 20 is believed to form a lamella structure 40 in water phase 12, building a gel structure to solidify the base.

The fact that the amphiphilic substance and the N-long chain acyl acidic amino acid monosalt associate and form a gel in water as well as the amount of the N-long chain acyl acidic amino acid monosalt and the amphiphilic substance present on the oil drop interface can be verified by DSC (differential scanning calorimetry) measurement. In the present invention, it is preferable that the amphiphilic substance and the N-long chain acyl acidic amino acid monosalt be present on the oil drop interface and that the amount present, measured by using the DSC peak area ratio, is 90% or more of the total content.

The total amount of said amphiphilic substance and the N-long chain acyl acidic amino acid monosalt is preferably 0.2 wt % or more of the water phase.

The blend ratio between the amphiphilic substance and the N-long chain acyl acidic amino acid monosalt can be adjusted at will, but the mole ratio is preferably 1:1–1:5, more preferably 1:2–1:4.

The amount of the inner phase oil in the O/W type emulsion is half or more, preferably an equal amount or more, of the total amount of the amphiphilic substance and the N-long chain acyl acidic amino acid monosalt. If the amount of the oil phase is less than half of the amphiphilic substance, then the emulsification stability over time tends to become poor.

The blend ratio of the amphiphilic substance is preferably 25 wt % or less, more preferably 10 wt % or less, of the total amount of the O/W type emulsion. The blend ratio of the N-long chain acyl acidic amino acid monosalt is preferably 20 wt % or less, more preferably 10 wt % or less of the total amount of the O/W type emulsion.

For the O/W type emulsion, the weight ratio of the oil phase: the water phase is preferably less than 1:1 so there is less of the oil phase.

Next, items which are common to the first and the second inventions of the present application are described below.

The organophilic modified clay mineral of the present invention is obtained by a quaternary ammonium salt type cation surfactant treatment of a water swelling clay mineral which is a type of colloidal hydrated aluminum silicate with a three-layer structure represented by the following general formula Chemical formula 1.

[Chemical Formula 1]

$$(X, Y)_{2-3}(Si, Al)_4O_{10}(OH)_2Z_{1/3} \cdot nH_2O$$

Where

X=Al, Fe(III), Mn(III), Cr(III),

Y=Mg, Fe(II), Ni, Zn, Li, and

Z=K, Na, Ca.

Specifically, it is obtained by a quaternary ammonium salt type cation surfactant treatment of a clay mineral such as natural or synthetic (in this case this refers to those whose (OH) groups in the formula are replaced by fluorine) montmorillonites including montmorillonite, saponite and hectorite, etc., (commercially available examples include beagum, kunipia and laponite) and synthetic mica known under names such as sodium silicic mica and sodium or lithium teniorite (commercially available examples include Daimonait from Topi Kogyo).

The quaternary ammonium salt type cation surfactant used in the present invention to modify the water swelling clay mineral to be organophilic is represented by the following general formula Chemical formula 2.

[Chemical Formula 2]

(In this formula, $R_1$ denotes a benzyl group or alkyl group with a carbon number of 10–22, $R_2$ denotes a methyl group or alkyl group with a carbon number of 10–22, $R_3$ and $R_4$ are hydroalkyl groups or alkyl groups with a carbon number of 1–3, and X denotes a halogen atom or methyl sulfate residue.)

Specific examples include dodecyltrimethylammonium chloride, myristyltrimethylammonium chloride, cetyltrimethylammonium chloride, stearyltrimethylammonium chloride, alkyltrimethylammonium chloride, behenyltrimethylammonium chloride, myristyltrimethylethylammonium chloride, cetyldimethylammonium chloride, stearyldimethylammonium chloride, arachildimethylammonium chloride, behenyldimethylammonium chloride, cetyldiethylammonium chloride, stearyldiethylammonium chloride, stearyldiethylammonium chloride, alkylidiethylammonium chloride, behenyldiethylammonium chloride, benzyldimethylmyristylammonium chloride, benzyldimethylcetylammonium chloride, benzyldimethylstearylammonium chloride, benzylmethylbehenylammonium chloride, benzylmethylethylcetylamonium chloride, benzyldimethylethylstearylammonium chloride, and dibehenylhydroxyethylammonium chloride, as well as the corresponding bromide and such, and dipalmitylpropylammonium methylsulfate, etc. When implementing the present invention, one or more are chosen from these at will.

For the organophilic modified clay minerals used in the present invention, the most preferable is to additionally use a nonionic surfactant during the aforementioned quaternary ammonium salt type cation surfactant treatment. Examples include ether type surfactants such as polyoxyethylene 2–30 mole adduct {hereafter abbreviated as POE (2–30)} oleyl ether, POE (2–35) stearyl ether, POE (2–20) lauryl ether, POE (1–20) alkylphenyl ether, POE (6–18) behenyl ether, POE (5–25) 2-decylpentadecyl ether, POE (3–30) 2-decyltetradecyl ether, and POE (8–16) 2-octyldecyl ether, ester type surfactants such as POE (4–60) hydrogenated castor oil, POE (3–14) fatty acid monoester, POE (6–30) fatty acid diester, and POE (5–20) sorbitan fatty acid ester, and ether ester type surfactants such as POE (2–30) glyceryl monoisostearate, POE (10–60) glyceryl triisostearate, POE (7–50) hydrogenated castor oil monoisostearate, and POE (12–60) hydrogenated castor oil triisostearate, which are ethyleneoxide adduct type surfactants, as well as glycerine fatty acid esters such as decaglyceryl tetraoleate, hexaglyceryl triisostearate, diglyceryl diisostearate, and glyceryl monooleate, etc., which are polyhydric alcohol fatty acid ester type surfactants. It is preferable to use one or more chosen from the group consisting of ethyleneoxide adduct type nonionic surfactants including polyglycerine fatty acid esters of diglycerine or higher such as decaglyceryl diisostearate, hexaglyceryl triisostearate, and diglyceryl diisostearate, POE adduct ether type surfactants such as POE (2–12) lauryl ether, POE (6–15) behenyl ether, POE (5–20) 2-decylpentadecyl ether, POE (5–17) 2-decyltetradecyl ether, etc., and POE (8–16) 2-octyldecyl ether, POE adduct ester type surfactants such as POE (10–20) hydrogenated castor oil, POE (5–14) oleic monoester, POE (6–20) oleic diester, and POE (5–10) sorbitan oleic ester, and POE adduct ether ester surfactants such as POE (3–15) glyceryl monoisostearate, and POE (10–40) glyceryl triisostearate.

The organophilic modified clay minerals used in the present invention can be obtained by dispersing/stirring the aforementioned water swelling clay minerals and the quaternary ammonium salt type cation surfactant (and the nonionic surfactant) in a solvent with a low boiling point, such as water, acetone, or lower alcohols, followed by removal of the solvent with a low boiling point.

The content of the quaternary ammonium salt type cation surfactant in the organophilic modified clay minerals is preferably 60–140 mili equivalents (hereafter abbreviated as "meq") for 100 g of the water swelling clay mineral.

Representative examples of the organophilic modified clay minerals preferably used in the present invention include dimethylalkylammonium hectorite, benzyldimethylstearylammonium hectorite, and aluminum magnesium silicate treated with distearyldimethyl ammonium chloride. Commercially available examples include Benton 38 (montmorillonite treated with distearyldimethylammonium chloride from National red Co.).

The blend ratio of the organophilic modified clay minerals is 0.1–10 wt %, preferably 0.5–5.0 wt %, of the total outer phase oil. If it is less than 0.1 wt % then the effect of the addition of the organophilic modified clay minerals cannot be achieved and a stable multiple emulsion cannot be obtained. If it is more than 10 wt % then the prepared O/W/O type multiple emulsion will have a high viscosity and poor spreadability, will be gritty, lack transparency, and so on, resulting in problems during actual use.

In addition to the aforementioned organophilic modified clay minerals, an emulsifying agent with a HLB of 7 or less must be blended in the outer phase oil. Examples include sorbitan fatty acid esters including the surfactants sorbitan monolaurate, sorbitan monooleate, sorbitan monoisostearate, and sorbitan tristearate, glycerine fatty acid esters including glycerol monostearate and glycerol monooleate, polyoxyethylene hydrogenated castor oils including POE (5), POE (7.5), and POE (10) hydrogenated castor oils, and polyether type silicon surfactants. Particularly preferable are polyether type silicone surfactants whose specific structure is represented by the following chemical formula 3.

[Chemical Formula 3]

(In this formula, R denotes a hydrogen atom or an alkyl group with a carbon number of 1–5, m denotes a number with an average of 1–150, n denotes a number with an average of 1–50, and a and b denote a number with an average of 0–35.)

The blend ratio of the emulsifying agent with a HLB of 7 or less is preferably 0.1–15 wt % of the total outer phase oil. The emulsifying agent with a HLB of 7 or less can be contained in the state of being adsorbed in the aforementioned essential ingredient organophilic modified clay minerals. That is, although the organophilic modified clay minerals and the emulsifying agent with a HLB of 7 or less are usually added separately when preparing the O/W/O type multiple emulsion, it is also possible to blend in the emulsifying agent with a HLB of 7 or less in the state of being adsorbed in the organophilic modified clay minerals by treating the organophilic modified clay minerals with a surfactant with a HLB of 7 or less which can be an emulsifying agent.

Examples of the oil ingredients used for the inner phase oil in the O/W type emulsion used in the present invention and the outer phase oil of the O/W/O type multiple emulsion of the present invention include liquid fat/oils including avocado oil, tsubaki oil, turtle oil, macademia nut oil, corn oil, mink oil, olive oil, rape seed oil, egg yolk oil, sesame seed oil, persic oil, wheat germ oil, sasanqua oil, castor oil, linseed oil, safflower oil, cotton seed oil, perilla oil, soy beam oil, peanut oil, tea seed oil, kaya oil, rice bran oil, chinese wood oil, Japanese wood oil, jojoba oil, germ oil, triglycerol, glyceryl trioctanoate and glyceryl triisopalmitate; solid fats/oils including cacao butter, coconut oil, horse tallow, hardened coconut oil, palm oil, beef tallow, sheep tallow, hardened beef tallow, palm kernel oil, pork tallow, beef bone tallow, Japanese core wax, hardened oil, neatsfoot tallow, Japanese wax and hydrogenated castor oil; waxes including beeswax, candelilla wax, cotton wax, carnauba wax, bayberry wax, tree wax, whale wax, montan wax, bran wax, lanolin, kapok wax, lanolin acetate, liquid lanolin, sugar cane wax, lanolin fatty acid isopropyl ester, hexyl laurate, reduced lanolin, jojoba wax, hard lanolin, shellac wax, POE lanolin alcohol ether, POE lanolin alcohol acetate, lanolin fatty acid polyethylene glycol and POE hydrogenated lanolin alcohol ether, etc.; hydrocarbons including liquid petrolatum, ozokerite, squalene, pristane, paraffin, ceresin, squalene, petrolatum and microcrystalline wax; synthetic esters including isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, lanolin acetate, isocetyl stearate, isocetyl isostearate, cholesteryl 12-hydroxystearate, ethylene glycol di-2-ethylhexylate, dipentaerythritol fatty acid ester, N-alkyl glycol monoisostearate, neopentyl glycol dicaprylate, diisostearyl malate, glyceryl di-2-heptylundecanoate, trimethylolpropane tri-2-ethylhexylate, trimethylolpropane triisostearate, pentaneerythritol tetra-2-ethylhexylate, glyceryl tri-2-ethylhexylate, trimethylolpropane triisostearate, cetyl 2-ethylhexanoate, 2-ethylhexyl palmitate, glyceryl trimyristate, tri-2-heptylundecanic acid glyceride, castor oil fatty acid methyl ester, oleyl oleate, cetostearyl alcohol, acetoglyceride, 2-heptylundecyl palmitate, diisopropyl adipate, 2-octyldodecyl N-lauroyl-L-glutamate, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, ethyl acetate, butyl acetate, amyl acetate and triethyl citrate, etc. In the present invention, the selection of the oil ingredients to be blended in is not limited and it is a marked advantage that solid and semi-solid oil ingredients can be contained in a stable manner.

In addition to these oil ingredients the following can also be blended in: chain polysiloxanes including dimethylpolysiloxane, methylphenylpolysiloxane, and methylhydrogenpolysiloxane, ring polysiloxanes including octamethylcyclotetrasiloxane, decamethylpolysiloxane, dodecamethylpolysiloxane, and tetramethyltetrahydrogenpolysiloxane, silicon oil such as modified silicon oils including amino modified silicone oil, epoxy modified silicone oil, epoxy/polyether modified silicone oil, polyether silicone oil, carboxy modified silicone oil, alcohol modified silicone oil, alkyl modified silicone oil, ammonium salt modified silicone oil, and fluorine modified silicone oil, silicone resins which form three-dimensional networks including trimethylsiloxysilicic acid, silicone resins such as high polymer methylpolysiloxane including high polymer dimethylpolysiloxane, higher polymer methylphenylpolysiloxane, etc., and high polymer methylvinylpolysiloxane, etc., and high polymer modified polysiloxane including high polymer amino modified methylpolysiloxane, etc., perfluorocarbons or perfluoropolyethers including perfluorodecalin, perfluorohexane, and triperfluoro-N-butylamine, vitamins including vitamin A and its derivatives, vitamin D and its derivatives, vitamin E and its derivatives, and vitamin K and its derivatives, sterols, and natural and synthetic perfumes.

Furthermore, substances which are hard to dissolve in water can be blended in the oil phase. Examples include ultraviolet light absorbents, preservatives such as paraben, vitamins such as ubiquinone and vitamin P, etc., disinfectants such as chlorohexydine hydrochloride, trichlorocarabanilide, and Irgasan DP300, and drugs such as dexamethasone acetate, etc.

The water phase which comprises the inner phase O/W type emulsion and the O/W/O type multiple emulsion of the present invention can contain water phase ingredients including water soluble active substances including vitamins such as the B vitamin group, vitamin C and its derivatives, pantothenic acid and its derivatives, and biotin, buffering agents such as sodium glutamate, arginine, aspartic acid, citric acid, tartaric acid, and lactic acid, chelating agents such as EDTA, water-soluble ultraviolet light absorbents, and various dyestuffs. Also, alcohols such as ethanol and isopropanol can also be blended in the water phase.

In the O/W/O type multiple emulsion of the present invention, the weight ratio between the inner phase O/W type emulsion and the outer oil is 2:3–19:1, preferably 3:2–17:3. If there is too much of the oil phase and the weight ratio between the O/W type emulsion and the oil phase becomes less than 2:3, then the obtained multiple emulsion will have a lower viscosity and the emulsification stability over time may deteriorate. If there is too much O/W type emulsion and the weight ratio between the O/W type emulsion and the oil phase becomes more than 19:1, then a phase conversion occurs during the stirring/emulsification, resulting in a mixture of the O/W/O type multiple emulsion and the O/W type emulsion, making it impossible to obtain the O/W/O type multiple emulsion of the present invention.

The following are specific examples of the ultraviolet light absorbents, polyhydric alcohols and other humectants which can be blended in the O/W/O type multiple emulsion of the present invention to give it a ultraviolet light absorbing effect and a moisture retaining effect.

Examples of the ultraviolet light absorbents are: benzoic acid type ultraviolet light absorbents including paraamino benzoic acid (hereafter abbreviated as PABA), PABA monoglycerine ester, N,N-dipropoxy PABA ethyl ester, N,N-diethoxy PABA ethyl ester, N,N-dimethyl PABA ethyl ester, N,N-dimethyl PABA butyl ester, N,N-dimethyl PABA methyl ester, and N,N-dimethyl PABA octyl ester; anthranilic acid type ultraviolet light absorbents including homomentyl-N-acetyl anthranilate; salicylic acid type ultraviolet light absorbents including amyl salicylate, mentyl salicylate, homomentyl salicylate, octyl salicylate, phenyl salicylate, benzyl salicylate and p-isopropanolphenyl salicylate, etc.; cinnamic acid type ultraviolet light absorbents including octyl cinnamate, ethyl-4-isopropylcinnamate, methyl-2,5-diisopropylcinnamate, ethyl-2,4-diisopropylcinnamate, methyl-2,4-diisopropylcinnamate, propyl-p-methoxycinnamate, isopropyl-p-methoxycinnamate, isoamyl-p-methoxycinnamate, octyl-p-methoxycinnamate, 2-ethylhexyl-p-methoxycinnamate, 2-ethoxyethyl-p-methoxycinnamate, cyclohexyl-p-methoxycinnamate, ethyl-α-cyano-β-phenylcinnamate, 2-ethylhexyl-α-cyano-β-phenylcinnamate and glyceryl mono-2-ethylhexanoyl-diparamethoxycinnamate etc.; benzophenone type ultraviolet light absorbents including 2,4-dihydroxy benzophenone, 2,2'-dihydroxy-4-methoxy benzophenone, 2,2'-dihydroxy-4,4'-dimethoxybenzophenone, 2,2',4,4'-tetrahydroxy benzophenone, 2-hydroxy-4-methoxy benzophenone, 2-hydroxy-4-methoxy-4'-methyl benzophenone, 2-hydroxy-4-methoxy benzophenone-5-sulfonate, 4-phenyl benzophenone, 2-ethylhexyl-4'-phenylbenzophenone-2-carboxylate, 2-hydroxy-4-N-octoxybenzophenone and 4-hydroxy-3-carboxybenzophenone; as well as 3-(4'-methylenzylidene)-d, 1-camphor, 3-benzylidene-d, 1-camphor, urocanic acid, ethyl urocanate, 2-phenyl-5-methyl benzoxazol, 2,2'-hydroxy-5-methylphenyl benzotriazol, 2-(2'-hydroxy-5'-t-octylphenyl) benzotriazol, 2-(2'-hydroxy-5'-methylphenyl benzotriazol, dibenzaladine, dianisoylmethane, 4-methoxy-4'-t-butyldibenzoylmethane and 5-(3,3-dimethyl-2-norbornylidene)-3-pentane-2-one.

Examples of the polyhydric alcohols follow: dihydric alcohols including ethylene glycol, propylene glycol, trimethylene glycol, 1,2-butylene glycol, 1,3-butylene glycol, tetramethylene glycol, 2,3-butylene glycol, pentamethylene glycol, 2-butene-1,4-diol, hexylene glycol and octylene glycol; trihydric alcohols including glycerol, trimethylolpropane and 1,2,6-hexanetriol, etc.; tetrahydric alcohols including pentaerythritol; pentahydric alcohols including xylitol; hexahydric alcohols including sorbitol and mannitol; polyhydric alcohol copolymers including diethylene glycol, dipropylene glycol, triethylene glycol, polypropylene glycol, triglycerol, tetraglycerol and polyglycerine, etc.; dihydric alcohol alkyl ethers including ethylene glycol monomethyl ether, ethylene glycol monoethyl ether, ethylene glycol monobutyl ether, ethylene glycol monophenyl ether, ethylene glycol monohexyl ether, ethylene glycol mono2-methylhexyl ether, ethylene glycol isoamyl ether, ethylene glycol benzyl ether, ethylene glycol isopropyl ether, ethylene glycol dimethyl ether, ethylene glycol diethyl ether and ethylene glycol dibutylether, etc.; dihydric alcohol alkyl ethers including diethylene glycol monometyl ether, diethylene glycol monoetyl ether, diethylene glycol monobutyl ether, diethylene glycol dimetyl ether, diethylene glycol dietyl ether, diethylene glycol dibutyl ether, diethylene glycol methylethyl ether, triethylene glycol monometyl ether, triethylene glycol monoetyl ether, propylene glycol monomethyl ether, propylene glycol monoethyl ether, propylene glycol monobutyl ether, propylene glycol isopropyl ether, dipropylene glycol methyl ether, dipropylene glycol ethyl ether and dipropylene glycol butyl ether; dihydric alcohol ether ester including ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate and propylene glycol monophenyl ether acetate.

Examples of the humectants include chondroitin sulfuric acid, hyaluronic acid, mucoitin sulfuric acid, charonic acid, soluble collagen, and cholesteryl-12-hydroxystearate, etc. Also, sodium lactate, bile acid monosalt, dl-pyrolidonecarboxylic acid monosalt, short chain soluble collagen, chestnut rose fruit extract, and yarrow extract can be blended in as long as the viscosity of the base is not lost.

The method for preparing the inner phase O/W type emulsion is not limited in particular and any method which gives a stable emulsion will suffice. For example, it can be prepared by adding a mixed dispersion containing the aforementioned essential ingredients, followed by stirring with an emulsifying device such as a homogenizer. A high pressure emulsification treatment or ultrasonic emulsification treatment using an emulsifying device which can exert strong shearing force such as Nanomizer, APV Gaulin, french press, colloid mill, micro-fluidizer, ultrasonic emulsifier, etc. makes the inner oil blend finely and stably, resulting in cream with a glossy smooth appearance. This is particularly preferable for the preparation of the O/W/O type multiple emulsion pertaining to the present invention.

The O/W/O type multiple emulsion of the present invention can be obtained by mixing/emulsifying the obtained O/W type emulsion while stirring in the outer phase oil containing the organophilic modified clay minerals and the emulsifying agent with a HLB of 7 or less. The selection of the emulsifying device to be used for this purpose is not limited in particular. Preferable are a disper (TK HOMD Disper from Tokushu Kika Kogyo Co., Ltc.) and such.

The applications of the O/W/O type multiple emulsion of the present invention are not limited in particular. Preferable applications include cosmetics, drugs, and quasi-drugs. It may be used for products such as creams, emulsions, and ointments.

EXAMPLES

The present invention is described in detail below by referring to examples. The present invention is not limited to these examples. The blend ratio is indicated in wt % units.

The blend ingredients shown in the following tables were used in a conventional method to prepare the O/W type emulsions of the Preparation examples and the O/W/O type multiple emulsions of the Examples and Comparative examples which used them. After letting stand for one month at room temperature or at 50° C., stability in storage was evaluated and usability was also evaluated by means of sensory evaluation by a panel of ten evaluation specialists using the following criteria.

[Stability in storage]

◎: Microscopic observation showed that the emulsified particles were uniform and no abnormality was observed.

○: Microscopic observation revealed some variation but no abnormality was visible to the naked eye.

Δ: Some variation of the emulsified particles was visible to the naked eye.

X: Oil separation and abnormalities such as enlargement of the emulsified particles were visible to the naked eye.

[Usability]

◎: All of the ten members in the evaluation specialist panel reported good "skin-compatibility" or "non-stickiness".

○: Eight or more and less than ten members in the evaluation specialist panel reported good "skin-compatibility" or "non-stickiness".

Δ: Six or more and less than eight members in the evaluation specialist panel reported good "skin-compatibility" or "non-stickiness".

X: Less than six members in the evaluation specialist panel reported good "skin-compatibility" or "non-stickiness".

"Preparation Examples 1–4: O/W type emulsion"

TABLE 1

| Blend ingredient/Preparation example | 1 | 2 | 3 | 4 |
| --- | --- | --- | --- | --- |
| (a) Amphiphilic substance and surfactant | | | | |
| Stearic acid | — | — | 2 | 2 |
| Behenic acid | — | — | 2 | 2 |
| Stearyl alcohol | — | — | 2 | 2 |
| Behenyl alcohol | — | — | 2 | 2 |
| POE (10) hydrogenated castor oil | 2 | 2 | — | — |
| (b) Oil phase | | | | |
| Liquid petrolatum | 20 | 16 | 10 | 10 |
| Petrolatum | — | 2 | 2 | 2 |
| Microcrystalline wax | — | 2 | 2 | 2 |
| Methyl paraben | 0.1 | 0.1 | 0.1 | 0.1 |
| Ethyl paraben | 0.1 | 0.1 | 0.1 | 0.1 |
| Butyl paraben | 0.1 | 0.1 | 0.1 | 0.1 |
| (c) Water phase | | | | |
| Ion exchanged water | Balance | Balance | Balance | Balance |
| 1,3 butylene glycol | 10 | 10 | 10 | 10 |

TABLE 1-continued

| Blend ingredient/Preparation example | 1 | 2 | 3 | 4 |
| --- | --- | --- | --- | --- |
| Polyethylene glycol | 2 | 2 | 2 | 2 |
| Caustic potash | — | — | 0.2 | 0.2 |
| Trehalose | 0.1 | 0.1 | 0.1 | 0.1 |

"Preparation method"

The (a) and (b) ingredients were mixed and homogeneously dissolved, to which the (c) ingredients were added, followed by stirring and emulsification. For Preparation examples 1–3, a homogenizer was used for emulsification. For Preparation 4, a Nanomizer was used for high pressure emulsification. In Preparations 3 and 4, a metal soap surfactant is produced in the recipe due to the reaction between stearic acid and behenic acid and caustic potash.

"Examples 1 and 2 and Comparative Examples 1 and 2: O/W/O type emulsion"

TABLE 2

| Blend ingredient/Comparative example & Example | Comparative example 1 | Comparative example 2 | Example 1 | Example 2 |
| --- | --- | --- | --- | --- |
| O/W type emulsion | | | | |
| Emulsion of the Preparation example 1 | 78 | — | — | — |
| Emulsion of the Preparation example 2 | — | 78 | — | — |
| Emulsion of the Preparation example 3 | — | — | 78 | — |
| Emulsion of the Preparation example 4 | — | — | — | 78 |
| Outer phase oil | | | | |
| Ring silicone oil | 20 | 20 | 20 | 20 |
| Emulsifying agent with a HLB of 7 or less | | | | |
| Dimethylsiloxane-methyl (POE) siloxane copolymer | 1 | 1 | 1 | 1 |
| Organophilic modified clay minerals | | | | |
| Benton 38 | 1 | 1 | 1 | 1 |
| [Stability in storage] | | | | |
| Room temperature | ○ | Δ | ○ | ◎ |
| 50° C. | ○ | X | ○ | ◎ |
| [Usability] | | | | |
| Skin-compatibility | Δ | Δ | ○ | ◎ |
| Non-stickiness | Δ | Δ | ○ | ◎ |

[Preparation method]

The ingredients were mixed and emulsified with a homogenizer to prepare the O/W/O type multiple emulsions.

Table 2 indicates that, even when solid and/or semi-solid oil ingredients are added, O/W/O type multiple emulsions with superior stability in storage and superior usability can be prepared in Examples 1 and 2 which use O/W type emulsions containing a higher alcohol, higher fatty acid and higher fatty acid soap. On the other hand, in Comparative examples 1 and 2, stable emulsions cannot be obtained and usability is not improved when solid and/or semi-solid oil ingredients were added for the purpose of improving usability. Example 2, which uses high pressure emulsification, has very good stability in storage and usability.

Next, using the same method as described above, all the O/W type multiple emulsions of preparation example 5–8 shown in Table 3 were prepared by using a Nanomizer for high pressure emulsification and the O/W/O type multiple emulsions shown in Table 4 were prepared. Comparative examples 3 and 4 use the amphiphilic substances and the surfactants in amounts which do not form a gel at ordinal temperature or higher in an amphiphilic substance-surfactant-oil-water system.

"Preparation Examples 5–8: O/W type emulsion"

TABLE 3

| Blend ingredient/ Preparation example | 5 | 6 | 7 | 8 |
| --- | --- | --- | --- | --- |
| (a) Amphiphilic substance and surfactant | | | | |
| Stearic acid | 1 | 0.1 | 1 | 0.5 |
| Behenic acid | 2 | 0.1 | 1 | 0.5 |
| Stearyl alcohol | 3 | 0.2 | 2 | 1 |
| Behenyl alcohol | 4 | 0.2 | 2 | 1 |
| (b) Oil phase | | | | |
| Methyl polysiloxane | 3 | 12.4 | 7 | 10 |
| Methyl paraben | 0.1 | 0.1 | 0.1 | 0.1 |
| Ethyl paraben | 0.1 | 0.1 | 0.1 | 0.1 |
| Butyl paraben | 0.1 | 0.1 | 0.1 | 0.1 |
| (c) Water phase | | | | |
| Ion exchanged water | Balance | Balance | Balance | Balance |
| Glycerine | 5 | 5 | 5 | 5 |
| Fructose | 2 | 2 | 2 | 2 |
| Caustic potash | 0.2 | 0.2 | 0.2 | 0.2 |

"Examples 3 and 4 and Comparative Examples 3 and 4: O/W/O type emulsion"

TABLE 4

| Blend ingredient/ Comparative example & Example | Comparative example 3 | Comparative example 4 | Example 3 | Example 4 |
| --- | --- | --- | --- | --- |
| O/W type emulsion | | | | |
| Emulsion of the Preparation example 5 | 78 | — | — | — |
| Emulsion of the Preparation example 6 | — | 78 | — | — |
| Emulsion of the Preparation example 7 | — | — | 78 | — |
| Emulsion of the Preparation example 8 | — | — | — | 78 |
| Outer phase oil | | | | |
| Ring silicone oil | 20 | 20 | 20 | 20 |
| Emulsifying agent with a HLB of 7 or less | | | | |
| Dimethylsiloxane-methyl (POE) siloxane copolymer | 1 | 1 | 1 | 1 |
| Organophilic modified clay minerals | | | | |
| Benton 38 | 1 | 1 | 1 | 1 |
| [Stability in storage] | | | | |
| Room temperature | X | Δ | ◎ | ◎ |
| 50° C. | X | X | ◎ | ◎ |

TABLE 4-continued

| Blend ingredient/ Comparative example & Example | Comparative example 3 | Comparative example 4 | Example 3 | Example 4 |
| --- | --- | --- | --- | --- |
| [Usability] | | | | |
| Skin-compatibility | X | X | ◎ | ◎ |
| Non-stickiness | X | X | ◎ | ◎ |

Examples 3 and 4 had very good stability in storage and usability, but Comparative example 3 developed aggregations of the solid oil ingredient and Comparative example 4 developed oil separation over time, and both had poor usability. As indicated by Comparative examples 3 and 4, even if the same amphiphilic substance and surfactant as those used in Examples 3 and 4 are used, O/W/O type multiple emulsions with good stability in storage and usability cannot be obtained when the blend ratios are such that a gel is not formed in the amphiphilic substance-surfactant-oil-water system at ordinal temperature or higher.

Using the same method as described above, all the O/W/O type multiple emulsions shown in Table 5 were prepared by using a Nanomizer for high pressure emulsification and the O/W/O type multiple emulsions shown in Table 6 were prepared. Comparative examples 5 and 6 both have a blend weight ratio between the O/W type emulsion and the outer phase oil which is outside of the range of the present invention.

TABLE 5

| Preparation example 9: O/W type emulsion | |
| --- | --- |
| Blend ingredient | Preparation example 9 |
| (a) Amphiphilic substance and surfactant | |
| Stearic acid | 1 |
| Behenic acid | 1 |
| Stearyl alcohol | 2 |
| Behenyl alcohol | 2 |
| (b) Oil phase | |
| Squalane | 5 |
| Pentaerythritol-2-ethylhexanoate | 2 |
| Vitamin E acetate | 0.1 |
| Butylhydroxy toluene | 0.05 |
| Methyl paraben | 0.1 |
| Ethyl paraben | 0.1 |
| Butyl paraben | 0.1 |
| (c) Water phase | |
| Ion exchanged water | Balance |
| 1,3 butylene glycol | 5 |
| Ethanol | 0.1 |
| Caustic potash | 0.2 |
| Erythritol | 1.0 |

"Examples 5–8 and Comparative Examples 5–6: O/W/O type emulsion"

Using the emulsion of Preparation 9 for the O/W type emulsion, the O/W/O type multiple emulsions of Examples 5–8 and Comparative examples 5–6 were prepared for evaluation in the same manner as the O/W/O type multiple emulsions shown in Table 2, except for the blend ratios between the O/W type emulsion and the outer phase oil which are shown in Table 6.

TABLE 6

| Example/Comparative example | Amount of O/W type emulsion | Amount of outer phase oil |
|---|---|---|
| Example 5 | 50 wt % | 50 wt % |
| Example 6 | 60 | 40 |
| Example 7 | 70 | 30 |
| Example 8 | 80 | 20 |
| Comparative example 5 | 35 | 65 |
| Comparative example 6 | 97 | 3 |

"Characteristic evaluation of the emulsions"

TABLE 7

| | Configuration of the emulsion (room temperature) | Stability in storage (room temperature) | Stability in storage (50° C.) |
|---|---|---|---|
| Example 5 | O/W/O | ○ | ○ |
| Example 6 | O/W/O | ◎ | ○ |
| Example 7 | O/W/O | ◎ | ◎ |
| Example 8 | O/W/O | ◎ | ○ |
| Comparative example 5 | O/W/O | X | X |
| Comparative example 6 | O/W/O + O/W | X | X |

Comparative example 5 had more oil phase than the amount which would make the weight ratio of the O/W type emulsion and the outer phase oil 2:3, and although an O/W/O type multiple emulsion was formed immediately following emulsification, the stability in storage was poor compared with Examples 5–8: oil separation was observed when stored at room temperature and also at 50° C. As shown in Comparative example 6, if there is more O/W type emulsion than the amount which would make the weight ratio of the O/W type emulsion and the outer phase oil 19:1, then a phase conversion occurs during the emulsification/ dispersing process and the prepared emulsion was verified to be a mixture of the O/W/O type and the O/W type.

"Preparation Examples 10–13: O/W type emulsion"

TABLE 8

| Blend ingredient/ Preparation example | 10 | 11 | 12 | 13 |
|---|---|---|---|---|
| (a) Amphiphilic substance and N-long chain acyl acidic amino acid monosalt, or surfactant | | | | |
| Behenyl alcohol | — | — | 4 | 4 |
| Sodium N-stearoyl-L-glutamate | — | — | 2 | 2 |
| POE (10) hydrogenated castor oil | 2 | 2 | — | — |
| (b) Oil phase | | | | |
| Liquid petrolatum | 20 | 16 | 12 | 12 |
| Petrolatum | — | 2 | 2 | 2 |
| Microcrystalline wax | — | 2 | 2 | 2 |
| Methyl paraben | 0.1 | 0.1 | 0.1 | 0.1 |
| Ethyl paraben | 0.1 | 0.1 | 0.1 | 0.1 |
| Butyl paraben | 0.1 | 0.1 | 0.1 | 0.1 |
| (c) Water phase | | | | |
| Ion exchanged water | Balance | Balance | Balance | Balance |
| 1,3 butylene glycol | 10 | 10 | 10 | 10 |
| NaCl | 0.5 | 0.5 | 0.5 | 0.5 |
| Arbutin | 2 | 2 | 2 | 2 |
| Trehalose | 0.1 | 0.1 | 0.1 | 0.1 |

[Preparation method]

The (a) and (b) ingredients were mixed and homogeneously dissolved, to which the (c) ingredients were added, followed by stirring and emulsification. For preparation examples 10–12, a homogenizer was used for emulsification. For preparation 4, a nanomizer was used for high pressure emulsification.

"Examples 9 and 10 and Comparative Examples 7 and 8: O/W/O type emulsion"

TABLE 9

| Blend ingredient/ Comparative example & Example | Comparative example 7 | Comparative example 8 | Example 9 | Example 10 |
|---|---|---|---|---|
| O/W type emulsion | | | | |
| Emulsion of the Preparation example 1 | 78 | — | — | — |
| Emulsion of the Preparation example 2 | — | 78 | — | — |
| Emulsion of the Preparation example 3 | — | — | 78 | — |
| Emulsion of the Preparation example 4 | — | — | — | 78 |
| Outer phase oil | | | | |
| Ring silicone oil | 20 | 20 | 20 | 20 |
| Emulsifying agent with a HLB of 7 or less | | | | |
| Dimethylsiloxane-methyl (POE) siloxane copolymer | 1 | 1 | 1 | 1 |
| Organophilic modified clay minerals | | | | |
| Benton 38 | 1 | 1 | 1 | 1 |
| [Stability in storage] | | | | |
| Room temperature | ○ | Δ | ○ | ◎ |
| 50° C. | ○ | X | ○ | ◎ |
| [Usability] | | | | |
| Skin-compatibility | Δ | Δ | ○ | ◎ |
| Non-stickiness | Δ | Δ | ○ | ◎ |

[Preparation method]

The ingredients were mixed and emulsified with a homogenizer to prepare the O/W/O type multiple emulsions.

Table 9 indicates that, even when solid and/or semi-solid oil ingredients are added, O/W/O type multiple emulsions with superior stability in storage and superior usability can be prepared in Examples 9 and 10 which use O/W type emulsions containing the amphiphilic substance and the N-long chain acyl acidic amino acid monosalt. On the other hand, in Comparative examples 7 and 8, stable emulsions cannot be obtained and usability is not improved when solid and/or semi-solid oil ingredients were added for the purpose of improving usability. Example 10, which uses high pressure emulsification, has very good stability in storage and usability.

Using the same method as described above, the O/W type multiple emulsions of Preparation examples 14–17 shown in Table 10 were all prepared by using a Nanomizer for high pressure emulsification and the O/W/O type multiple emulsions shown in Table 11 were prepared. Comparative examples 9 and 10 use the amphiphilic substances and the surfactants in amounts which do not form a gel at ordinal temperature or higher in an amphiphilic substance-surfactant-oil-water system.

"Preparation Examples 14–17: O/W Type Emulsion"

TABLE 10

| Blend ingredient/ Preparation example | 14 | 15 | 16 | 17 |
|---|---|---|---|---|
| (a) Amphiphilic substance and N-long chain acyl acidic amino acid monosalt | | | | |
| Stearyl alcohol | 3 | 0.2 | 2 | 1 |
| Behenyl alcohol | 4 | 0.2 | 2 | 1 |
| N-stearoyl-L-glutamic acid monosalt | 1 | 1 | 1 | 1 |
| (b) Oil phase | | | | |
| Methyl polysiloxane | 3 | 12.4 | 7 | 10 |
| Methyl paraben | 0.1 | 0.1 | 0.1 | 0.1 |
| Ethyl paraben | 0.1 | 0.1 | 0.1 | 0.1 |
| Butyl paraben | 0.1 | 0.1 | 0.1 | 0.1 |
| (c) Water phase | | | | |
| Ion exchanged water | Balance | Balance | Balance | Balance |
| Glycerine | 5 | 5 | 5 | 5 |
| Sodium L-arginate | 2 | 2 | 2 | 2 |
| Fructose | 2 | 2 | 2 | 2 |

"Examples 11 and 12 and Comparative Examples 9 and 10: O/W/O Type Emulsion"

TABLE 11

| Blend ingredient/ Comparative example & Example | Comparative example 9 | Comparative example 10 | Example 11 | Example 12 |
|---|---|---|---|---|
| O/W type emulsion | | | | |
| Emulsion of the Preparation example 5 | 78 | — | — | — |
| Emulsion of the Preparation example 6 | — | 78 | — | — |
| Emulsion of the Preparation example 7 | — | — | 78 | — |
| Emulsion of the Preparation example 8 | — | — | — | 78 |
| Outer phase oil | | | | |
| Ring silicone oil | 20 | 20 | 20 | 20 |
| Emulsifying agent with a HLB of 7 or less | | | | |
| Dimethylsiloxane-methyl (POE) siloxane copolymer | 1 | 1 | 1 | 1 |
| Organophilic modified clay minerals | | | | |
| Benton 38 | 1 | 1 | 1 | 1 |
| [Stability in storage] | | | | |
| Room temperature | X | Δ | ⊚ | ⊚ |
| 50° C. | X | X | ⊚ | ⊚ |

TABLE 11-continued

| Blend ingredient/ Comparative example & Example | Comparative example 9 | Comparative example 10 | Example 11 | Example 12 |
|---|---|---|---|---|
| [Usability] | | | | |
| Skin-compatibility | X | X | ⊚ | ⊚ |
| Non-stickiness | X | X | ⊚ | ⊚ |

Examples 11 and 12 had very good stability in storage and usability, but Comparative example 9 developed aggregations of the solid oil ingredient and Comparative example 10 developed oil separation over time, and both had poor usability. As indicated by Comparative examples 9 and 10, even if the same amphiphilic substance and N-long chain acyl acidic amino acid monosalt as those used in Examples 11 and 12 are used, O/W/O type multiple emulsions with good stability in storage and usability cannot be obtained when the blend ratios are such that a gel is not formed in the amphiphilic substance-N-long chain acyl acidic amino acid monosalt-oil-water system at ordinal temperature or higher.

Using the same method as described above, all the O/W type multiple emulsions of Preparation example 18 shown in Table 12 were prepared by using a Nanomizer for high pressure emulsification and the O/W/O type multiple emulsions shown in Table 13 were prepared. Comparative examples 11 and 12 both have a blend weight ratio between the O/W type emulsion and the outer phase oil which is outside of the range of the present invention.

TABLE 12

Preparation example 18: O/W type emulsion

| Blend ingredient | Preparation example 18 |
|---|---|
| (a) Amphiphilic substance and N-long chain acyl acidic amino acid monosalt | |
| Cetanol | 8 |
| Sodium N-stearoyl-L-glutamate | 5 |
| (b) Oil phase | |
| Squalane | 5 |
| Pentaerythritol-2-ethylhexanoate | 2 |
| Vitamin E acetate | 0.1 |
| Butylhydroxy toluene | 0.05 |
| Methyl paraben | 0.1 |
| Ethyl paraben | 0.1 |
| Butyl paraben | 0.1 |
| (c) Water phase | |
| Ion exchanged water | Balance |
| 1,3 butylene glycol | 5 |
| Ethanol | 0.1 |
| Erythritol | 1.0 |

"Examples 13–16 and Comparative Examples 11–12: O/W/O Type Emulsion"

Using the emulsion of Preparation 18 for the O/W type emulsion, the O/W/O type multiple emulsions of Examples 13–16 and Comparative examples 11–12 were prepared for evaluation in the same manner as the O/W/O type multiple emulsions shown in Table 9, except for the blend ratios between the O/W type emulsion and the outer phase oil which are shown in Table 13.

TABLE 13

| Example/Comparative example | Amount of O/W type emulsion | Amount of outer phase oil |
|---|---|---|
| Example 13 | 50 wt % | 50 wt % |
| Example 14 | 60 | 40 |
| Example 15 | 70 | 30 |
| Example 16 | 80 | 20 |
| Comparative example 11 | 35 | 65 |
| Comparative example 12 | 97 | 3 |

"Characteristic Evaluation of the Emulsions"

TABLE 14

| | Configuration of the emulsion (room temperature) | Stability in storage (room temperature) | Stability in storage (50° C.) |
|---|---|---|---|
| Example 13 | O/W/O | ○ | ○ |
| Example 14 | O/W/O | ⊙ | ○ |
| Example 15 | O/W/O | ⊙ | ⊙ |
| Example 16 | O/W/O | ⊙ | ○ |
| Comparative example 11 | O/W/O | X | X |
| Comparative example 12 | O/W/O + O/W | X | X |

Comparative example 11 had more oil phase than the amount which would make the weight ratio of the O/W type emulsion and the outer phase oil 2:3, and although an O/W/O type multiple emulsion was formed immediately following emulsification, the stability in storage was poor compared with Examples 13–16: oil separation was observed when stored at room temperature and also at 50° C. As shown in Comparative example 6, if there is more O/W type emulsion than the amount which would make the weight ratio of the O/W type emulsion and the outer phase oil 19:1, then a phase conversion occurs during the emulsification/dispersing process and the prepared emulsion was verified to be a mixture of the O/W/O type and the O/W type.

INDUSTRIAL APPLICABILITY OF THE INVENTION

According to the present invention, an O/W/O type multiple emulsion with superior stability over time and good usability can be obtained.

What is claimed is:

1. An O/W/O type multiple emulsion in which an O/W type emulsion is dispersed in the outer phase oil wherein the O/W type emulsion in the inner phase contains water, an oil based ingredient, a surfactant and an amphiphilic substance chosen from the group consisting of those which can form a gel at ordinal temperature or higher in an amphiphilic substance-surfactant-oil-water system, said outer phase oil contains organophilic modified clay minerals and an emulsifying agent with a HLB of 7 or lower, and the weight ratio of the O/W type emulsion and the outer phase oil is 2:3–19:1.

2. The O/W/O type multiple emulsion of claim 1 wherein said amphiphilic substance is composed of a higher fatty acid and/or higher alcohol whose carbon chain has a carbon number of 12 or more.

3. The O/W/O type multiple emulsion of claim 2 wherein the surfactant contained in said inner phase O/W type emulsion is composed of a metal soap of a higher fatty acid.

4. The O/W/O type multiple emulsion of claim 2 wherein said organophilic modified clay minerals are obtained by treating a water swelling clay mineral with a quaternary ammonium type cation surfactant and a nonionic surfactant.

5. The O/W/O type multiple emulsion of claim 2 wherein the amphiphilic substance contained in the O/W type emulsion dispersed in said outer phase oil is a higher alcohol and higher fatty acid, the surfactant is a metal soap prepared by neutralizing said higher fatty acid, and said amphiphilic substance is contained in the inner phase oil of the O/W type emulsion in the amount of 0.1–80 wt %.

6. A method of preparing the O/W/O type multiple emulsion of claim 2, comprising a process in which the oil based ingredient which is to be the inner oil is added to an aqueous solution containing a neutralizing agent and the O/W type emulsion is prepared by a high pressure emulsification treatment or an ultrasonic emulsification treatment and a process in which said O/W type emulsion is dispersed and emulsified in the oil based ingredient which is to be the outer phase oil and contains an organophilic modified clay minerals and an emulsifying agent with a HLB of 7 or less.

7. The O/W/O type multiple emulsion of claim 1 wherein the surfactant contained in said inner phase O/W type emulsion is composed of a metal soap of a higher fatty acid.

8. The O/W/O type multiple emulsion of claim 7 wherein said organophilic modified clay minerals are obtained by treating a water swelling clay mineral with a quaternary ammonium type cation surfactant and a nonionic surfactant.

9. The O/W/O type multiple emulsion of claim 7 wherein the amphiphilic substance contained in the O/W type emulsion dispersed in said outer phase oil is a higher alcohol and higher fatty acid, the surfactant is a metal soap prepared by neutralizing said higher fatty acid, and said amphiphilic substance is contained in the inner phase oil of the O/W type emulsion in the amount of 0.1–80 wt %.

10. A method of preparing the O/W/O type multiple emulsion of claim 7, comprising a process in which the oil based ingredient which is to be the inner oil is added to an aqueous solution containing a neutralizing agent and the O/W type emulsion is prepared by a high pressure emulsification treatment or an ultrasonic emulsification treatment and a process in which said O/W type emulsion is dispersed and emulsified in the oil based ingredient which is to be the outer phase oil and contains an organophilic modified clay minerals and an emulsifying agent with a HLB of 7 or less.

11. The O/W/O type multiple emulsion of claim 1 wherein said organophilic modified clay minerals are obtained by treating a water swelling clay mineral with a quaternary ammonium type cation surfactant and a nonionic surfactant.

12. The O/W/O type multiple emulsion of claim 11 wherein the amphiphilic substance contained in the O/W type emulsion dispersed in said outer phase oil is a higher alcohol and higher fatty acid, the surfactant is a metal soap prepared by neutralizing said higher fatty acid, and said amphiphilic substance is contained in the inner phase oil of the O/W type emulsion in the amount of 0.1–80 wt %.

13. A method of preparing the O/W/O type multiple emulsion of claim 11, comprising a process in which the oil based ingredient which is to be the inner oil is added to an aqueous solution containing a neutralizing agent and the O/W type emulsion is prepared by a high pressure emulsification treatment or an ultrasonic emulsification treatment and a process in which said O/W type emulsion is dispersed and emulsified in the oil based ingredient which is to be the outer phase oil and contains an organophilic modified clay minerals and an emulsifying agent with a HLB of 7 or less.

14. The O/W/O type multiple emulsion of claim 1 wherein the amphiphilic substance contained in the O/W type emulsion dispersed in said outer phase oil is a higher alcohol and higher fatty acid, the surfactant is a metal soap prepared by neutralizing said higher fatty acid, and said amphiphilic substance is contained in the inner phase oil of the O/W type emulsion in the mount of 0.1–80 wt %.

15. A method of preparing the O/W/O type multiple emulsion of claim 14, comprising a process in which the oil based ingredient which is to be the inner oil is added to an aqueous solution containing a neutralizing agent and the O/W type emulsion is prepared by a high pressure emulsification treatment or an ultrasonic emulsification treatment and a process in which said O/W type emulsion is dispersed and emulsified in the oil based ingredient which is to be the outer phase oil and contains an organophilic modified clay minerals and an emulsifying agent with a HLB of 7 or less.

16. A method of preparing the O/W/O type multiple emulsion of claim 1 comprising a process in which the oil based ingredient which is to be the inner oil is added to an aqueous solution containing a neutralizing agent and the O/W type emulsion is prepared by a high pressure emulsification treatment or an ultrasonic emulsification treatment and a process in which said O/W type emulsion is dispersed and emulsified in the oil based ingredient which is to be the outer phase oil and contains an organophilic modified clay minerals and an emulsifying agent with a HLB of 7 or less.

17. An O/W/O type multiple emulsion in which an O/W type emulsion is dispersed in the outer phase oil wherein the O/W type emulsion in the inner phase contains water, an oil based ingredient, N-long chain acyl acidic amino acid monosalt and an amphiphilic substance chosen from the group consisting of those which can form a gel at ordinal temperature or higher in an amphiphilic substance-N-long chain acyl acidic amino acid monosalt-oil-water system, said outer phase oil contains organophilic modified clay minerals and an emulsifying agent with a HLB of 7 or lower, and the weight ratio of the O/W type emulsion and the outer phase oil is 2:3–19:1.

18. The O/W/O type multiple emulsion of claim 17 wherein said amphiphilic substance is composed of a higher fatty acid and/or higher alcohol whose carbon chain has a carbon number of 12 or more.

19. The O/W/O type multiple emulsion of claim 18 wherein the N-long chain acyl acidic amino acid monosalt contained in said inner phase O/W type emulsion is N-stearoyl-L-glutamic acid monosalt.

20. The O/W/O type multiple emulsion of claim 18 wherein said inner phase O/W type emulsion contains an N-long chain acyl acidic amino acid disalt and its content is such that the mole ratio is 0.25 or less of that of the N-long chain acyl acidic amino acid monosalt.

21. The O/W/O type multiple emulsion of claim 18 wherein the content of the inner phase oil in the O/W type emulsion is half or more of the total of said amphiphilic substance and N-long chain acyl acidic amino acid monosalt.

22. The O/W/O type multiple emulsion of claim 18 wherein said amphiphilic substance and the N-long chain acyl acidic amino acid monosalt are present on the oil drop interface of the O/W type emulsion and the amount, measured by using the DSC peak area ratio, is 90% or more of the total content.

23. The O/W/O type multiple emulsion of claim 18 wherein the total amount of said amphiphilic substance and the N-long chain acyl acidic amino acid monosalt is 0.2 wt % or more of the water phase of the O/W type emulsion.

24. The O/W/O type multiple emulsion of claim 18 wherein said organophilic modified clay minerals are obtained by treating a water swelling clay mineral with a quaternary ammonium type cation surfactant and a nonionic surfactant.

25. A method of preparing the O/W/O type multiple emulsion of claim 18 comprising a process in which the oil based ingredient which is to be the inner oil is added to the water phase containing an N-long chain acyl acidic amino acid monosalt and then the O/W type emulsion is prepared by a high pressure emulsification treatment or an ultrasonic emulsification treatment and a process in which said O/W type emulsion is dispersed and emulsified in the oil based ingredient which is to be the outer phase oil and contains an organophilic modified clay minerals and an emulsifying agent with a HLB of 7 or less.

26. The O/W/O type multiple emulsion of claim 17 wherein the N-long chain acyl acidic amino acid monosalt contained in said inner phase O/W type emulsion is N-stearoyl-L-glutamic acid monosalt.

27. The O/W/O type multiple emulsion of claim 26 wherein said inner phase O/W type emulsion contains an N-long chain acyl acidic amino acid disalt and its content is such that the mole ratio is 0.25 or less of that of the N-long chain acyl acidic amino acid monosalt.

28. The O/W/O type multiple emulsion of claim 26 wherein the content of the inner phase oil in the O/W type emulsion is half or more of the total of said amphiphilic substance and N-long chain acyl acidic amino acid monosalt.

29. The O/W/O type multiple emulsion of claim 26 wherein said amphiphilic substance and the N-long chain acyl acidic amino acid monosalt are present on the oil drop interface of the O/W type emulsion and the amount, measured by using the DSC peak area ratio, is 90% or more of the total content.

30. The O/W/O type multiple emulsion of claim 26 wherein the total amount of said amphiphilic substance and the N-long chain acyl acidic amino acid monosalt is 0.2 wt % or more of the water phase of the O/W type emulsion.

31. The O/W/O type multiple emulsion of claim 26 wherein said organophilic modified clay minerals are obtained by treating a water swelling clay mineral with a quaternary ammonium type cation surfactant and a nonionic surfactant.

32. A method of preparing the O/W/O type multiple emulsion of claim 26 comprising a process in which the oil based ingredient which is to be the inner oil is added to the water phase containing an N-long chain acyl acidic amino acid monosalt and then the O/W type emulsion is prepared by a high pressure emulsification treatment or an ultrasonic emulsification treatment and a process in which said O/W type emulsion is dispersed and emulsified in the oil based ingredient which is to be the outer phase oil and contains an organophilic modified clay minerals and an emulsifying agent with a HLB of 7 or less.

33. The O/W/O type multiple emulsion of claim 17 wherein said inner phase O/W type emulsion contains an N-long chain acyl acidic amino acid disalt and its content is such that the mole ratio is 0.25 or less of that of the N-long chain acyl acidic amino acid monosalt.

34. The O/W/O type multiple emulsion of claim 33 wherein the content of the inner phase oil in the O/W type emulsion is half or more of the total of said amphiphilic substance and N-long chain acyl acidic amino acid monosalt.

35. The O/W/O type multiple emulsion of claim 33 wherein said amphiphilic substance and the N-long chain acyl acidic amino acid monosalt are present on the oil drop interface of the O/W type emulsion and the amount, measured by using the DSC peak area ratio, is 90% or more of the total content.

36. The O/W/O type multiple emulsion of claim 33 wherein the total amount of said amphiphilic substance and the N-long chain acyl acidic amino acid monosalt is 0.2 wt % or more of the water phase of the O/W type emulsion.

37. The O/W/O type multiple emulsion of claim 33 wherein said organophilic modified clay minerals are obtained by treating a water swelling clay mineral with a quaternary ammonium type cation surfactant and a nonionic surfactant.

38. A method of preparing the O/W/O type multiple emulsion of claim 33 comprising a process in which the oil based ingredient which is to be the inner oil is added to the water phase containing an N-long chain acyl acidic amino acid monosalt and then the O/W type emulsion is prepared by a high pressure emulsification treatment or an ultrasonic emulsification treatment and a process in which said O/W type emulsion is dispersed and emulsified in the oil based ingredient which is to be the outer phase oil and contains an organophilic modified clay minerals and an emulsifying agent with a HLB of 7 or less.

39. The O/W/O type multiple emulsion of claim 17 wherein the content of the inner phase oil in the O/W type emulsion is half or more of the total of said amphiphilic substance and N-long chain acyl acidic amino acid monosalt.

40. The O/W/O type multiple emulsion of claim 39 wherein said amphiphilic substance and the N-long chain acyl acidic amino acid monosalt are present on the oil drop interface of the O/W type emulsion and the amount, measured by using the DSC peak area ratio, is 90% or more of the total content.

41. The O/W/O type multiple emulsion of claim 39 wherein the total amount of said amphilic substance and the N-long chain acyl acidic amino acid monosalt is 0.2 wt % or more of the water phase of the O/W type emulsion.

42. The O/W/O type multiple emulsion of claim 39 wherein said organophilic modified clay minerals are obtained by treating a water swelling clay mineral with a quaternary ammonium type cation surfactant and a nonionic surfactant.

43. A method of preparing the O/W/O type multiple emulsion of claim 39 comprising a process in which the oil based ingredient which is to be the inner oil is added to the water phase containing an N-long chain acyl acidic amino acid monosalt and then the O/W type emulsion is prepared by a high pressure emulsification treatment or an ultrasonic emulsification treatment and a process in which said O/W type emulsion is dispersed and emulsified in the oil based ingredient which is to be the outer phase oil and contains an organophilic modified clay minerals and an emulsifying agent with a HLB of 7 or less.

44. The O/W/O type multiple emulsion of claim 17 wherein said amphiphilic substance and the N-long chain acyl acidic amino acid monosalt are present on the oil drop interface of the O/W type emulsion and the amount, measured by using the DSC peak area ratio, is 90% or more of the total content.

45. The O/W/O type multiple emulsion of claim 44 wherein the total amount of said amphiphilic substance and the N-long chain acyl acidic amino acid monosalt is 0.2 wt % or more of the water phase of the O/W type emulsion.

46. The O/W/O type multiple emulsion of claim 44 wherein said organophilic modified clay minerals are obtained by treating a water swelling clay mineral with a quaternary ammonium type cation surfactant and a nonionic surfactant.

47. A method of preparing the O/W/O type multiple emulsion of claim 44 comprising a process in which the oil based ingredient which is to be the inner oil is added to the water phase containing an N-long chain acyl acidic amino acid monosalt and then the O/W type emulsion is prepared by a high pressure emulsification treatment or an ultrasonic emulsification treatment and a process in which said O/W type emulsion is dispersed and emulsified in the oil based ingredient which is to be the outer phase oil and contains an organophilic modified clay minerals and an emulsifying agent with a HLB of 7 or less.

48. The O/W/O type multiple emulsion of claim 17 wherein the total amount of said amphiphilic substance and the N-long chain acyl acidic amino acid monosalt is 0.2 wt % or more of the water phase of the O/W type emulsion.

49. The O/W/O type multiple emulsion of claim 48 wherein said organophilic modified clay minerals are obtained by treating a water swelling clay mineral with a quaternary ammonium type cation surfactant and a nonionic surfactant.

50. A method of preparing the O/W/O type multiple emulsion of claim 48 comprising a process in which the oil based ingredient which is to be the inner oil is added to the water phase containing an N-long chain acyl acidic amino acid monosalt and then the O/W type emulsion is prepared by a high pressure emulsification treatment or an ultrasonic emulsification treatment and a process in which said O/W type emulsion is dispersed and emulsified in the oil based ingredient which is to be the outer phase oil and contains an organophilic modified clay minerals and an emulsifying agent with a HLB of 7 or less.

51. The O/W/O type multiple emulsion of claim 17 wherein said organophilic modified clay minerals are obtained by treating a water swelling clay mineral with a quaternary ammonium type cation surfactant and a nonionic surfactant.

52. A method of preparing the O/W/O type multiple emulsion of claim 51 comprising a process in which the oil based ingredient which is to be the inner oil is added to the water phase containing an N-long chain acyl acidic amino acid monosalt and then the O/W type emulsion is prepared by a high pressure emulsification treatment or an ultrasonic emulsification treatment and a process in which said O/W type emulsion is dispersed and emulsified in the oil based ingredient which is to be the outer phase oil and contains an organophilic modified clay minerals and an emulsifying agent with a HLB of 7 or less.

53. A method of preparing the O/W/O type multiple emulsion of claim 17 comprising a process in which the oil based ingredient which is to be the inner oil is added to the water phase containing an N-long chain acyl acidic amino acid monosalt and then the O/W type emulsion is prepared by a high pressure emulsification treatment or an ultrasonic emulsification treatment and a process in which said O/W type emulsion is dispersed and emulsified in the oil based ingredient which is to be the outer phase oil and contains an organophilic modified clay minerals and an emulsifying agent with a HLB of 7 or less.

* * * * *